(12) United States Patent
Herrin (10) Patent No.: US 10,779,850 B2
(45) Date of Patent: Sep. 22, 2020

(54) ROTATIONAL TISSUE CUTTING CONTROL DEVICE (71) Applicant: Spiration, Inc., Redmond, WA (US)

(72) Inventor: David A. Herrin, Seattle, WA (US)

(73) Assignee: Gyrus ACMI, Inc., Southborough, MA (US)

(*) Notice: Subject to any disclaimer, the term of this patent is extended or adjusted under 35 U.S.C. 154(b) by 253 days.

(21) Appl. No.: 15/933,363

(22) Filed: Mar. 22, 2018

(65) Prior Publication Data

US 2019/0290313 A1 Sep. 26, 2019

(51) Int. Cl.
A61B 17/32 (2006.01)
A61B 17/3201 (2006.01)
A61B 17/3207 (2006.01)
A61B 17/00 (2006.01)

(52) U.S. Cl.
CPC .... *A61B 17/3201* (2013.01); *A61B 17/32002* (2013.01); *A61B 17/320758* (2013.01); *A61B 2017/00367* (2013.01)

(58) Field of Classification Search
CPC .............. A61B 17/147; A61B 17/1615; A61B 17/1624; A61B 17/1637; A61B 17/1642; A61B 17/3201; A61B 17/32002; A61B 17/320758; B23B 41/12; B23B 51/108
See application file for complete search history.

(56) References Cited

U.S. PATENT DOCUMENTS

| | | | | |
|---|---|---|---|---|
| 8,465,491 B2 * | 6/2013 | Yedlicka | ............ | A61B 17/1615 606/80 |
| 8,690,793 B2 * | 4/2014 | Ranpura | ............ | A61B 10/0275 600/562 |
| 9,216,459 B2 * | 12/2015 | Richt | .................... | B23B 45/008 |

* cited by examiner

*Primary Examiner* — Sarah W Aleman
(74) *Attorney, Agent, or Firm* — Clements Bernard Walker (57) ABSTRACT

Disclosed embodiments include apparatuses and systems for controlling an apparatus for cutting an opening in a tissue wall. In an illustrative embodiment, an apparatus for controlling a counter-rotatable cutting apparatus includes a first radial actuator configured to engage a first drive shaft. A second radial actuator is configured to engage a second drive shaft, the second drive shaft being coaxially disposed with the first drive shaft. A housing supports the first radial actuator and the second radial actuator and permits the first drive shaft and the second drive shaft to extend therethrough, the first drive shaft and the second drive shaft being relatively counter-rotatable responsive to rotation of at least one of the first radial actuator and the second radial actuator.

19 Claims, 10 Drawing Sheets

ROTATIONAL TISSUE CUTTING CONTROL DEVICE

CROSS-REFERENCE TO RELATED APPLICATION

The present application is related to "ROTATIONAL TISSUE CUTTING DEVICE" filed herewith, the entire contents of which are incorporated by reference.

FIELD

The present disclosure relates to apparatuses, systems, and methods for cutting an opening in a tissue wall.

BACKGROUND

The statements in this section merely provide background information related to the present disclosure and may not constitute prior art.

The ability to access tissues within a patient's body without invasive surgery allows for ever-improving types of analysis, diagnosis, and treatment with reduced pain, reduced recovery time, and a reduced risk of complications. By way of two examples, endoscopic imaging and catherization treatments have enabled evaluation and treatment of numerous internal lesions without invasive surgery.

In some cases, it may be desirable to insert a thin, probe-like device to remotely cut tissue within a patient's body. For example, to provide a patient with relief when a bile duct becomes blocked, it would be desirable to insert a probe into the gastronomical tract to cut an opening to enable the gall bladder to discharge bile into the duodenum to relieve painful swelling of the gall bladder. However, although it may be possible to insert a probe to reach the desired location, it may prove very difficult to remotely make a small cut. The tissues may be too pliable to punch or cut through when there is no structure behind the tissue to press against in making the cut.

SUMMARY

Disclosed embodiments include apparatuses, systems, and methods for cutting an opening in a tissue wall.

In an illustrative embodiment, an apparatus includes an inner cutting member having a first cylindrical body supporting at least one first cutting surface at a distal end. The first cutting surface faces a first rotational direction relative to an axis of the first cylindrical body and has a first cutting edge at an outer periphery of the first cylindrical body. The apparatus also includes an outer cutting member having a second cylindrical body concentrically disposed around the first cylindrical body and supporting at least one second cutting surface at the distal end. The second cutting surface faces a second rotational direction relative to the axis and has a second cutting edge at an inner periphery of the second cylindrical body. A tissue is rotatably scissorable between the first cutting edge of the inner cutting member and the second cutting edge of the outer cutting member responsive to application of the distal end of the apparatus against a tissue and counter-rotating the inner cutting member and the outer cutting member.

In another illustrative embodiment, an apparatus includes an inner cutting member having a first cylindrical body supporting two or more first cutting surfaces at a distal end of the apparatus. The first cutting surfaces face a first rotational direction relative to an axis of the first cylindrical body. The first cutting surface includes a first cutting edge at an outer periphery of the first cylindrical body and inclined relative to the axis of the inner cutting member. The first cutting surface also includes an anchor tip extending outwardly beyond the distal end and configured to pierce the tissue. The apparatus also includes an outer cutting member having a second cylindrical body concentrically disposed around the first cylindrical body and supporting at least one second cutting surface at the distal end of the apparatus. The second cutting surface faces a second rotational direction relative to the axis and has a second cutting edge at an inner periphery of the second cylindrical body. A tissue is pierceable by the anchor tip and is rotationally scissorable between the first cutting edge of the inner cutting member and the second cutting edge of the outer cutting member responsive to application of the distal end of the apparatus against a tissue and counter-rotating the inner cutting member and the outer cutting member.

In a further illustrative embodiment, a method includes extending a cylindrical cutting apparatus having an inner cutting member and a concentric outer cutting member against a tissue. The inner cutting member and the concentric outer cutting member have opposed cutting surfaces configured to radially cut the tissue orthogonally to an axis of the inner cutting member and the concentric outer cutting member. An inner cutting member is moved to cause an anchor tip at a distal end of the inner cutting member to pierce the tissue. The inner cutting member and the concentric outer cutting member are rotated relative to one another to radially cut the tissue.

In another illustrative embodiment, an apparatus for controlling a counter-rotatable cutting apparatus includes a first radial actuator configured to engage a first drive shaft. A second radial actuator is configured to engage a second drive shaft, the second drive shaft being coaxially disposed with the first drive shaft. A housing supports the first radial actuator and the second radial actuator and permits the first drive shaft and the second drive shaft to extend therethrough, the first drive shaft and the second drive shaft being relatively counter-rotatable responsive to rotation of at least one of the first radial actuator and the second radial actuator.

In a further illustrative embodiment, an apparatus for controlling a counter-rotatable cutting apparatus includes a first radial actuator configured to engage a first drive shaft. A second radial actuator is configured to engage a second drive shaft, the second drive shaft being coaxially disposed with the first drive shaft. A counter-rotating mechanism mechanically couples the first radial actuator and the second radial actuator, the counter-rotating mechanism being configured to cause the second radial actuator to rotate in a second direction when the first radial actuator is turned in a first direction. A housing supports the first radial actuator and the second radial actuator and permitting the first drive shaft and the second drive shaft to extend therethrough. A rotation control is mechanically coupled with the first radial actuator to permit rotation of the first radial actuator, the first drive shaft and the second drive shaft being simultaneously counter-rotatable responsive to rotation of the first rotation control.

In still another illustrative embodiment, a system for cutting an opening in a tissue wall includes a drive shaft assembly that includes a first drive shaft, a second drive shaft coaxially disposed around the first drive shaft and configured to rotate independently of the first drive shaft, and a sheath containing the first drive shaft and the second drive shaft. A first radial actuator is configured to engage the first drive shaft. A second radial actuator is configured to engage the second drive shaft. A housing supports the first radial actuator and the second radial actuator and permits the sheath containing the first drive shaft and the second drive shaft to extend therethrough. A rotation control is mechanically coupled with the first radial actuator to permit rotation of the first radial actuator relative to the second radial actuator. A cutting apparatus includes an inner cutting member having a first cylindrical body supporting at least one first cutting surface at a distal end of the cutter and is mechanically coupled to the first drive shaft, where the first cutting surface faces a first rotational direction relative to an axis of the first cylindrical body and has a first cutting edge at an outer periphery of the first cylindrical body. An outer cutting member having a second cylindrical body is concentrically disposed around the first cylindrical body and is mechanically coupled with the second drive shaft, where the outer cutting member supports at least one second cutting surface at the distal end of the apparatus and the second cutting surface faces a second rotational direction relative to the axis and has a second cutting edge at an inner periphery of the second cylindrical body. A tissue is rotatably scissorable between the first cutting edge of the inner cutting member and the second cutting edge of the outer cutting member responsive to application of the distal end of the apparatus and rotation of the rotation control.

Further features, advantages, and areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way. The components in the figures are not necessarily to scale, with emphasis instead being placed upon illustrating the principles of the disclosed embodiments. In the drawings:

FIGS. 4A-5C are perspective and side views of embodiments of an outer cutting member of the cutting apparatus of FIG. 2;

DETAILED DESCRIPTION

The following description is merely illustrative in nature and is not intended to limit the present disclosure, application, or uses. It will be noted that the first digit of three-digit reference numbers and the first two digits of four-digit reference numbers correspond to the first digit of one-digit figure numbers and the first two-digits of the figure numbers, respectively, in which the element first appears.

The following description explains, by way of illustration only and not of limitation, various embodiments of apparatuses, systems, and methods for cutting tissue. As will be described in detail below, a cutting apparatus having rotating elements capable of counter-rotation are extended to a tissue and caused to rotate relative to each other to pierce and scissor tissue.

Figure 1:
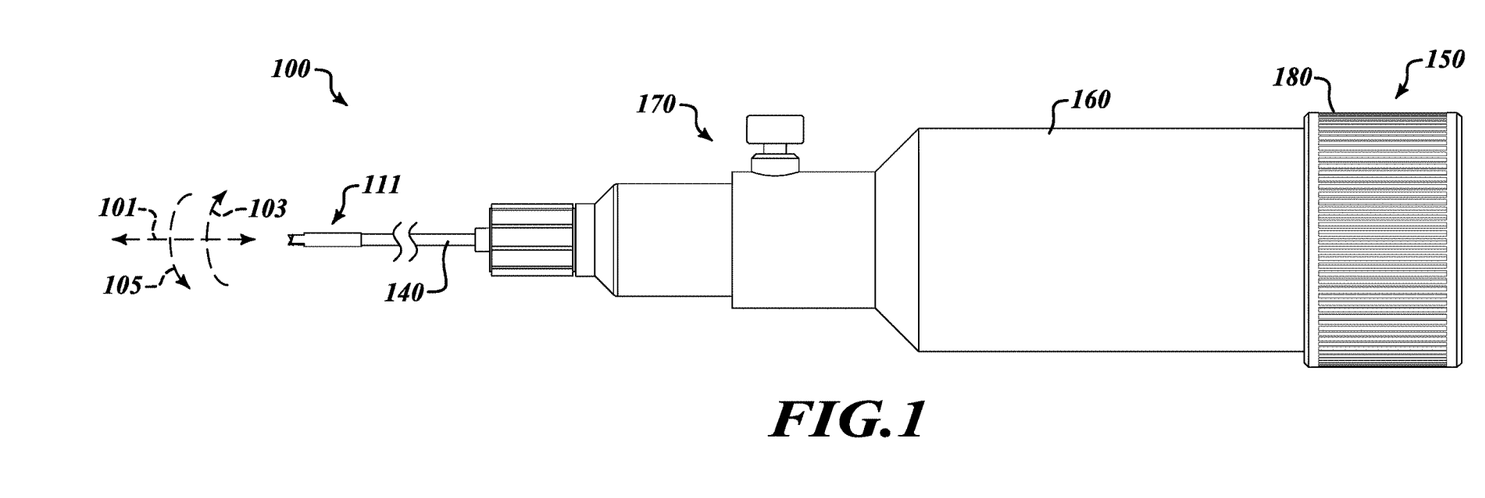
FIG. 1 is a side plan view of a system for cutting tissue according to the present disclosure.

Referring to FIG. 1, an illustrative system 100 is provided for cutting an opening in a tissue wall in an anatomical region of a patient (not shown in FIG. 1). In various embodiments, the system 100, in general, includes a cutting apparatus 111, a control apparatus 150 for controlling the cutting apparatus 111, and a drive shaft assembly 140 coupling the cutting apparatus 111 with the control apparatus 150. As will be described in detail below, the cutting apparatus 111 is a counter-rotatable cutting apparatus having cutting members configured to rotate in directions 103 or 105 about an axis 101, as described further below with reference to FIGS. 2, 3A-3C, 4A-4C, 5A-5C, and 6. The drive shaft assembly 140 includes a first drive shaft and a second drive shaft which, in some embodiments, includes a hollow shaft coaxially disposed around the first drive shaft. The first drive shaft and the second drive shaft are couplable with members of the cutting apparatus 111 and contained in a sheath, as further described below with reference to FIG. 11. In some embodiments, the first drive shaft and the second drive shaft include flexible, counter-rotatable cables. The control apparatus 150 includes a housing 160 that supports a position adjustment apparatus 170 and at least one rotation grip 180, each of which is further described below with reference to FIGS. 7, 8, and/or 9.

Figure 2:
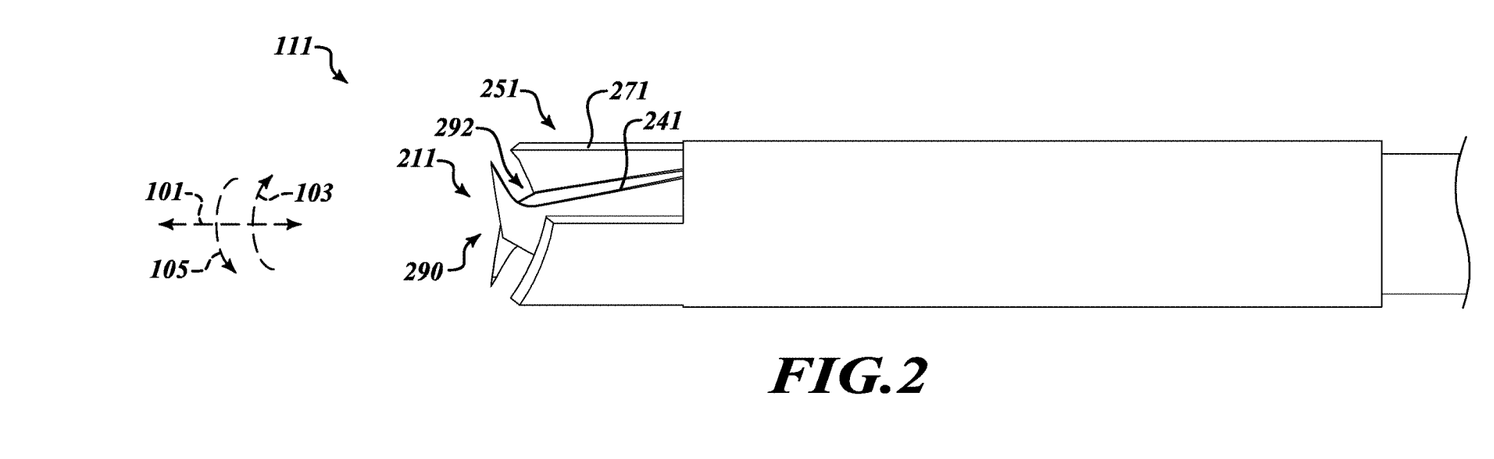
FIG. 2 is a side plan view of a cutting apparatus of the system of FIG. 1.

Referring to FIG. 2, the cutting apparatus 111 includes two counter-rotatable members including an inner cutting member 211 and an outer cutting member 251. As described further below with reference to FIGS. 3A-3C and 5A-5C, the inner cutting member 211 is configured to pierce and/or secure tissue at a distal end 290 at the cutting apparatus 211 and then to draw the tissue into a cutting region 292 between opposing cutting surfaces including an inner cutting surface 241 on the inner cutting member 211 and an outer cutting surface 271 on the outer cutting member 251. Counter-rotation of the inner cutting member 211 and the outer cutting member 251 thus scissors the tissue to form an opening in the tissue.

Figure 3A:
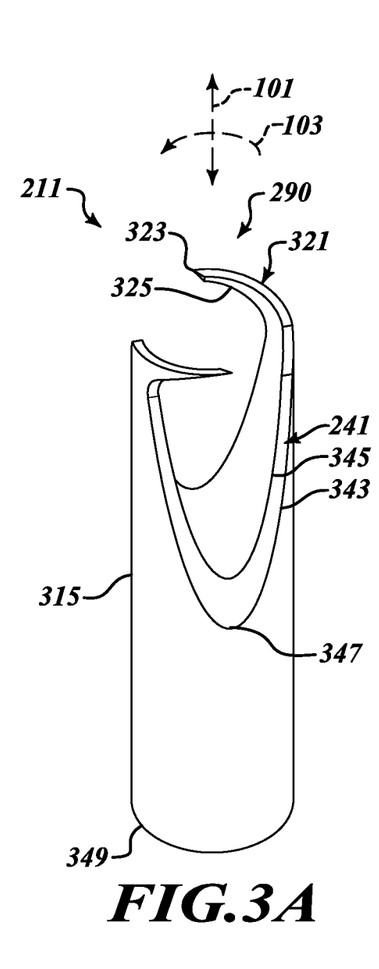
FIGS. 3A-3C are perspective and side views of an inner cutting member of the cutting apparatus of FIG. 2.
Figure 3B:
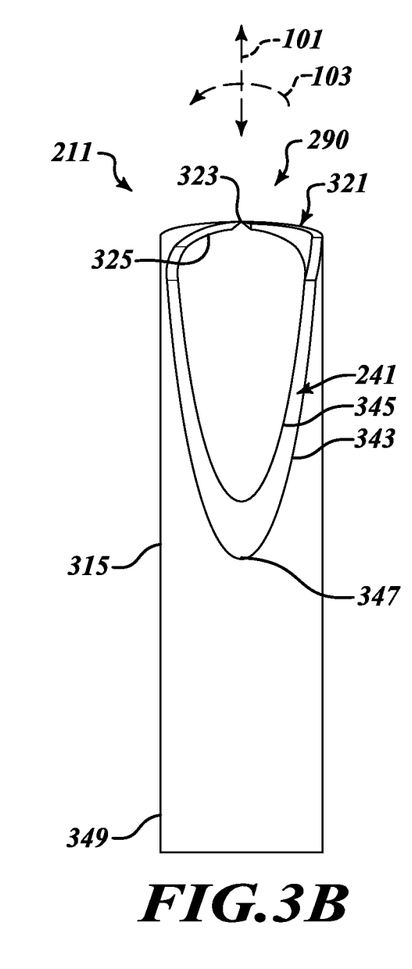
Figure 3C:
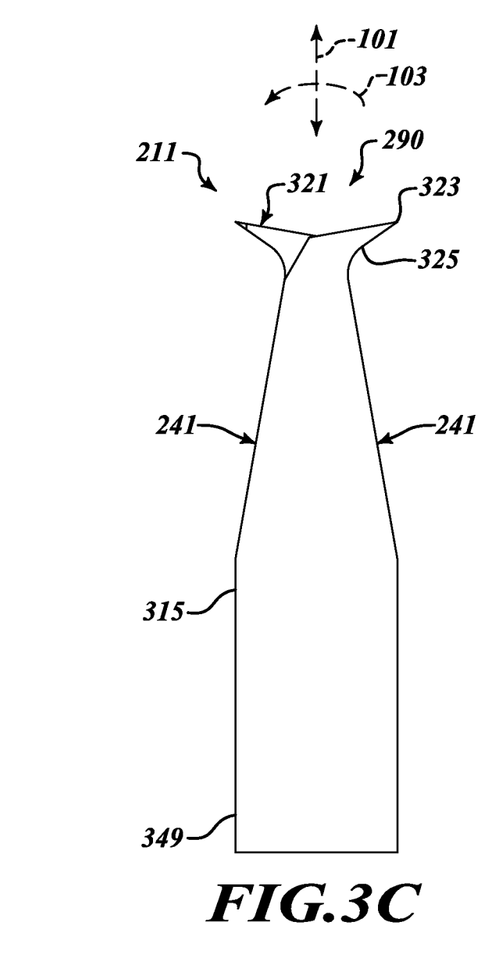

Referring to FIGS. 3A-3C, the inner cutting member 211 includes a body 315 having a proximal end 349 that engages the drive shaft assembly 140 (FIG. 1; not shown in FIGS. 3A-3C) which is further described below with reference to FIG. 11. The inner cutting member 211 includes one or more anchor tips 321 extending longitudinally toward the distal end 290 and curving radially around an axis 101 in a direction 103. The anchor tips 321 are angled so as extend forward of the one or more inner cutting surfaces 241 toward the distal end 290. The anchor tips 321 have a piercing end 323 configured to pierce a tissue wall (not shown in FIGS.

3A-3C) presented at the distal end 290 of the inner cutting member 211. In some embodiments and as shown in FIGS. 2, 3A-3C, and 6, the anchor tips 321 describe a helical shape. In some other embodiments, the anchor tips 321 also may include a flattened anchoring surface 325 facing away from the distal end 290.

The inner cutting member 211 also includes the one or more inner cutting surfaces 241. The inner cutting surfaces 241 are inclined from a leading cutting edge 343 to a trailing cutting edge 345. In some embodiments, the leading cutting edge 343 of the inner cutting surface 241 is at an outer edge of the inner cutting member where it will engage a leading edge of the outer cutting surface 271 of the outer cutting member 251, as further described below. In some embodiments, the one or more inner cutting surfaces 241 are inclined at an acute angle relative to the axis 101. The one or more inner cutting surfaces 241 are so angled such that, in the cutting region 292 (FIG. 2), the one or more inner cutting surfaces 241 of the inner cutting member and one or more inner cutting surfaces 271 of the outer cutting member 251 come together at an acute angle facing the distal end 290 like the opposing blades of a pair of scissors, thereby facilitating scissoring of the tissue. The inner cutting surface 241 of the inner cutting member 211 is parabolically shaped, terminating at a lower end 347 to help form a scissor shape between the inner cutting surfaces 241 and the outer cutting surfaces 271.

Continuing to refer to FIGS. 3A-3C, presenting the anchor tip 321 against a tissue wall and rotating the inner cutting member 211 around the axis 101 in the direction 103 will cause the piercing end 323 of the anchor tip 321 to pierce the tissue. Continued rotation around the axis 101 in the direction 103 then may cause the flattened anchoring surface 325 to lever the tissue wall away from the distal end 290 and into the cutting region 292. In the cutting region, the inner cutting surface 241 will scissor the tissue against the outer cutting surface 271 (FIG. 2) as previously described and as further described below with reference to FIG. 6.

Figure 4A:
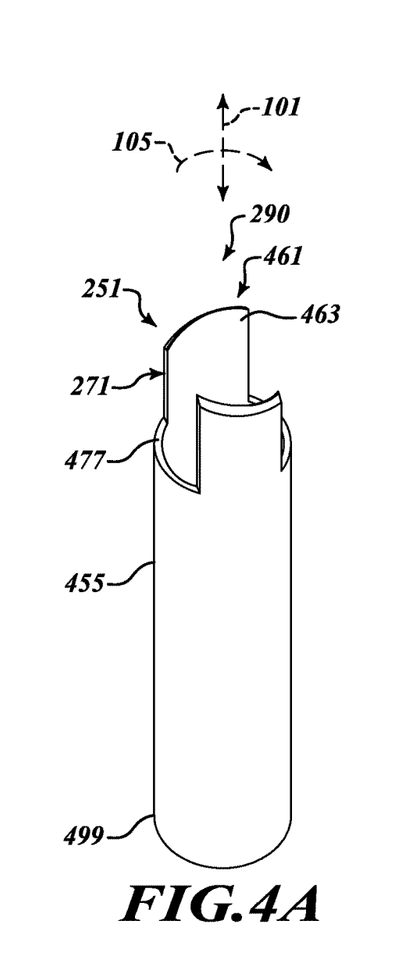
Figure 4B:
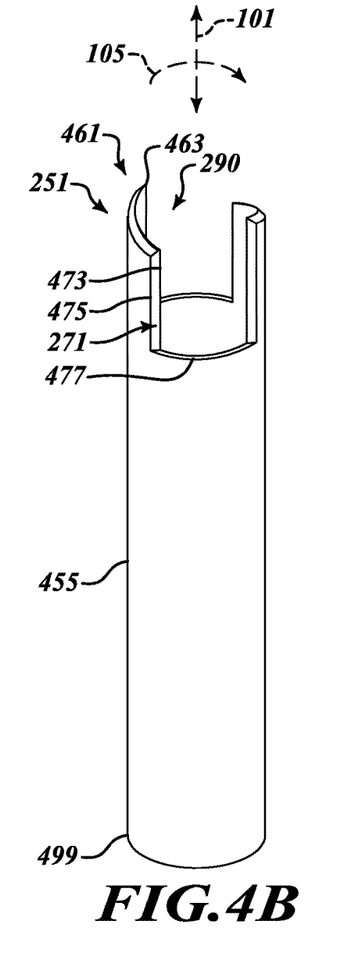
Figure 4C:
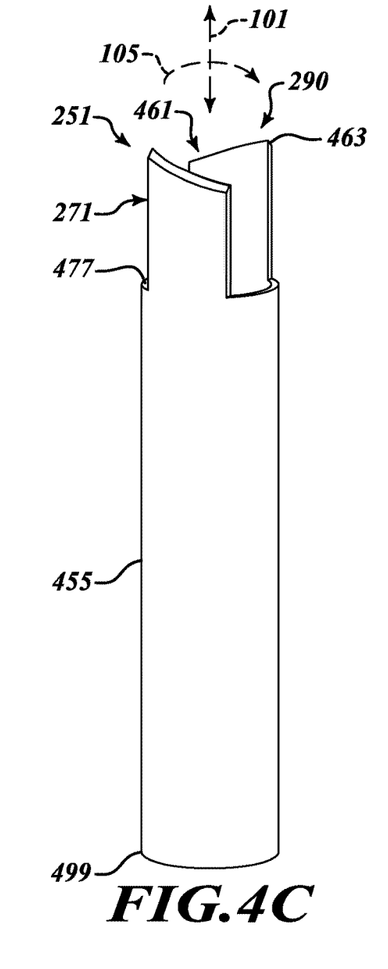

Referring to FIGS. 4A-4C, the outer cutting member 251 includes a body 455 having a proximal end 499 that engages the drive shaft assembly 140 (FIG. 1; not shown in FIGS. 4A-4C) which is further described below with reference to FIG. 11. The outer cutting member 251 includes a leading end 461 which, in some embodiments, includes a pointed end 463 extending both longitudinally toward the distal end 290. In some embodiments, the leading end 461 angles away from the pointed end 463 at the distal end 290 to facilitate penetration into a tissue wall as further described with reference to FIG. 6. The outer cutting member 251 also includes one or more outer cutting surfaces 271. The outer cutting surfaces 271 are inclined from a leading cutting edge 473 to a trailing cutting edge 475. In some embodiments, the leading cutting edge 473 of the outer cutting surface 271 is at an inner edge of the outer cutting member 251 where it will engage a leading edge 343 of the inner cutting surface 241 of the inner cutting member 221, as further described below with reference to FIG. 6.

In some embodiments, the outer cutting surface 271 of the outer cutting member 251 is generally U-shaped, terminating at a lower end 477. As shown in FIGS. 4A-4C, in some embodiments the outer cutting surfaces 271 are substantially parallel with the axis 101. Presenting the outer cutting member 251 along with the inner cutting member (FIGS. 2 and 3A-3C) against a tissue wall and counter-rotating the outer cutting member 251 in the second direction 105 around the axis 101 against the inner cutting member 211 will scissor the tissue between the outer cutting surface 271 of the outer cutting member 251 and the inner cutting surface 241 of the inner cutting member 211, as will be further described below with reference to FIG. 6.

In some embodiments and as shown in FIGS. 3A-3C and FIGS. 4A-4C, the inner cutting surfaces 241 are acutely angled relative to the axis 101 and the outer cutting surfaces 271 are substantially parallel with the axis 101 to present opposing cutting surfaces that intersect at an acute angle to facilitate the scissoring of tissue. However, it will be appreciated that the same acute cutting angle between opposing cutting surfaces could be formed by arranging the inner cutting surfaces 241 of the inner cutting member 211 substantially parallel with the axis 101, while acutely angling the outer cutting surfaces 271 relative to the axis 101 to form an acute cutting angle between the cutting surfaces 241 and 271. Further, in some other embodiments the inner cutting surfaces 214 of the inner cutting member 211 and the outer cutting surfaces 271 of the outer cutting member 251 could both be angled—in opposite directions—from the axis 101 to form an acute cutting angle between the opposing cutting surfaces 241 and 271. Also, as previously described with reference to FIGS. 3A-3C and 4A-4C, the leading edge 343 of the inner cutting surfaces 241 of the inner cutting member 221 are at an outer surface of the inner cutting member 221 and the leading edge 473 of the outer cutting surfaces 471 of the outer cutting member 251 are at an inner surface of the outer cutting member 251 so that the leading edges 343 and 473 will come together like the leading edges of scissor blades to facilitate scissoring tissue therebetween.

Figure 5A:
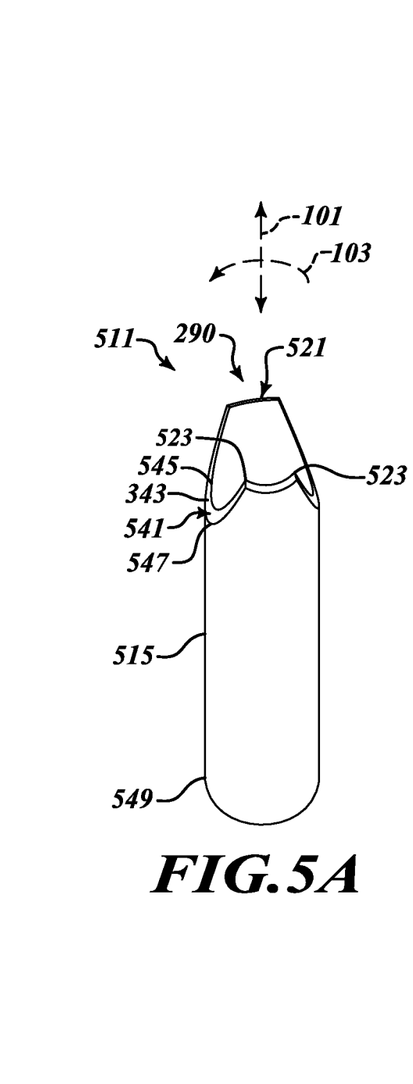
FIGS. 5A-5C are perspective and side views of another embodiment of an inner cutting member of the cutting apparatus of FIG. 2.
Figure 5B:
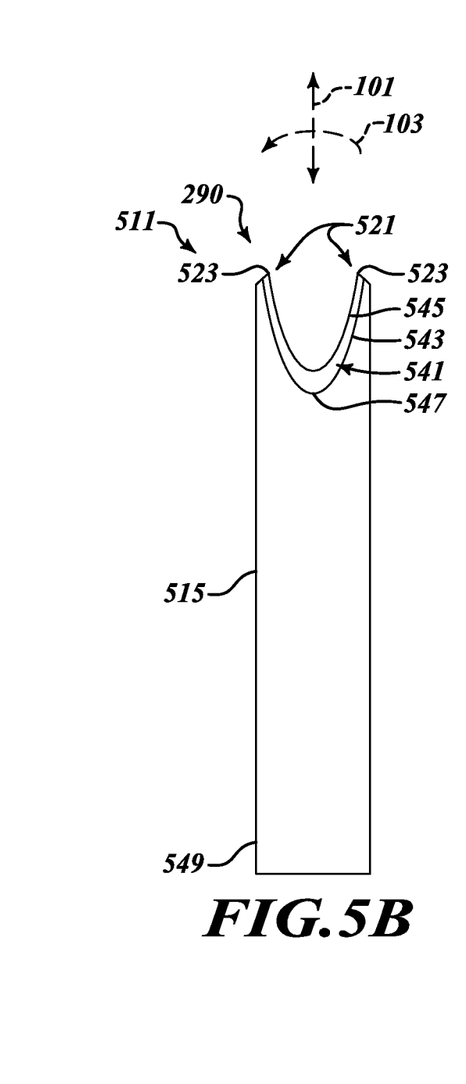
Figure 5C:
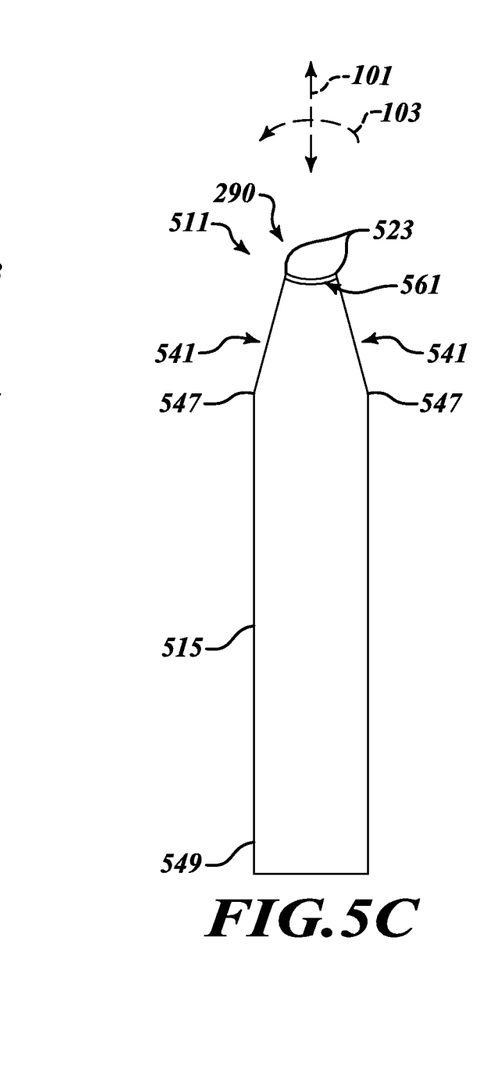

Referring to FIGS. 5A-5C, in some other embodiments the inner cutting member 511 includes a body 515 having a proximal end 549 that engages the drive shaft assembly 140 (FIG. 1; not shown in FIGS. 3A-3C) which is further described below with reference to FIG. 10. Instead of the angled anchor tips 321 of the inner cutting member 211 as shown in FIGS. 2 and 3A-3C, the inner cutting member 511 includes concave anchor tips 521 having a pair of piercing ends 523 at either end. The piercing ends 523 are configured to pierce a tissue wall (not shown in FIGS. 5A-5C) presented at the distal end 290 of the inner cutting member 511. The anchor tips 521 would thus hold the tissue as the outer cutting member 251 is counter-rotated against the inner cutting member 511. The inner cutting member 511 and an outer cutting member (not shown) then may be relatively counter-rotated to scissor tissue between the inner cutting surfaces. In some embodiments, the inner cutting surfaces 541, including the leading edges 543, trailing edges 545, and a generally parabolic shape terminating at a lower end 547, are like those of the corresponding leading edges 343, trailing edges 345, and a generally parabolic shape terminating at a lower end 347 of the inner cutting member 211 as shown in FIGS. 2 and 3A-3C. It should be noted, however, that the inner cutting surfaces 541 may be differently angled relative to the axis 101 to correspond with angling of the outer cutting surfaces 271 as previously described with reference to FIGS. 4A-4C to form a scissor-type shape between the inner cutting surfaces 541 and the outer cutting surfaces 271.

Figure 6:
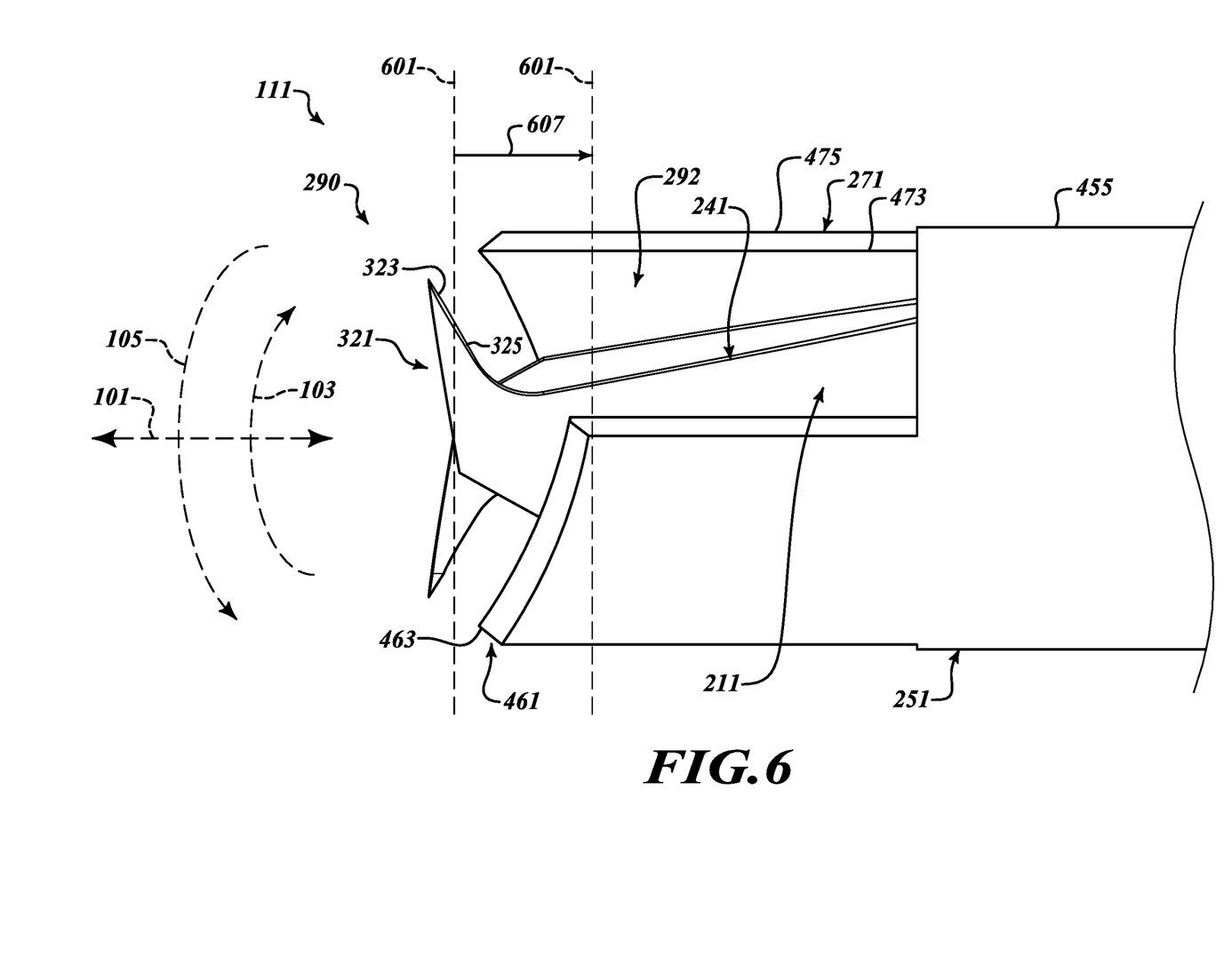
FIG. 6 is an enlarged side plan view of the cutting apparatus of FIG. 2.

In various embodiments and referring to FIG. 6, the cutting apparatus 111, including the inner cutting member 211 and the outer cutting member 251, is positioned and operated to pierce and scissor tissue. The cutting apparatus 111 is positioned at a tissue wall 601, represented by a dashed line. The inner cutting member 211 and the outer cutting member 251 are relatively counter-rotated, with the inner cutting member 211 relatively counter-rotating in the first direction 103 about the axis 101 and the outer cutting member 251 relatively counter-rotating in the second direction 105 about the axis 101. Rotation of the inner cutting member 321 in the first direction 103 causes the piercing ends 323 of the anchor tips 321 to pierce the tissue wall 601. Further relatively counter-rotating the inner cutting member 211 causes the flattened anchoring surfaces 325 facing away from the distal end 290 of the cutting apparatus 111 to lever tissue at the tissue wall 601 in a direction 607 into the cutting region 292.

As the cutting members 211 and 251 of the cutting apparatus 111 move relative to one another, the tissue wall 601 is drawn between the inner cutting surfaces 241 of the inner cutting member 211 and the outer cutting surfaces 271 of the outer cutting member 251. As the inner cutting member 211 and the outer cutting member 251 are relatively counter-rotated about the axis 101, the inner cutting surfaces 241 and the outer cutting surfaces 271 scissor the tissue 601 about the periphery of the cutting apparatus 111 to form an opening in the tissue wall 601.

In some other embodiments in which the inner cutting member includes the cutting apparatus 111, such as the inner cutting member 511 as shown in FIGS. 5A-5C, the anchor tips 521 of the inner cutting member 511 may not be configured to lever the tissue into a cutting region between cutting surfaces as will the anchor tips 221 of the inner cutting member 211 (FIGS. 2, 3A-3C, and 6). However, pressure applied by the cutting apparatus 111 toward the distal end 290 of the cutting apparatus 111 against the tissue wall 601 may result in piercing of the cutting apparatus 111 into the tissue wall 601 and movement of the cutting apparatus 111 into the tissue wall to bring the tissue into the cutting range 292 between the inner cutting surfaces 541 of the inner cutting member 511 and the outer cutting surfaces 271 of the outer cutting member 251.

Figure 7:
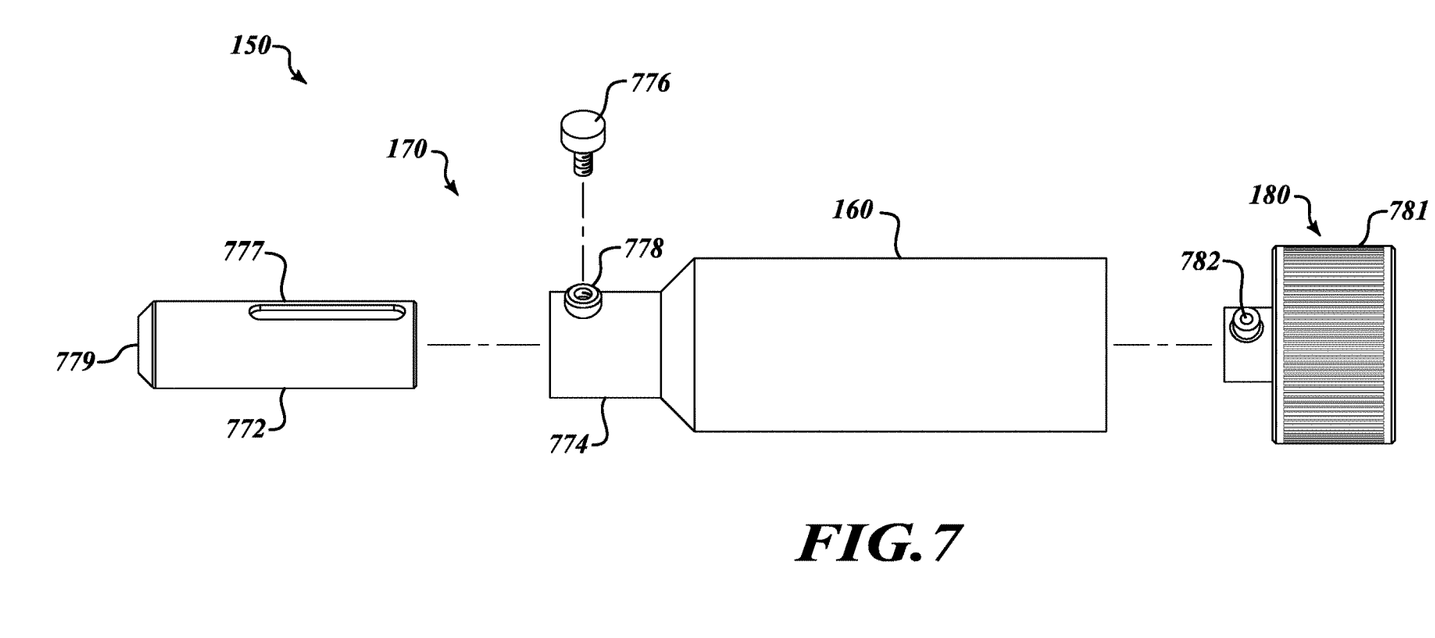
FIG. 7 is an exploded view of an embodiment of an apparatus for controlling a counter-rotatable cutting apparatus of the system of FIG. 1.

Referring to FIG. 7, in various embodiments the control apparatus 150 includes components that may be used to position and relatively counter-rotate the cutting apparatus 111 (not shown in FIG. 7). A position adjustment apparatus 170 includes a sleeve 772 fixably joined to a sheath of a drive shaft assembly 140 (not shown in FIG. 7) which then extends from a first end 779 of the sleeve 772 facing a direction where the cutting apparatus 111 is to be deployed. The sleeve 772 is slideably receivable into a first end 774 of the housing 160 of the control apparatus 150. The sleeve 772 includes a locking groove 777 that receives a sheath lock 776 that, in turn, is received through a sheath locking port 778 in the housing 160.

As shown in FIG. 7, in some embodiments the sheath lock 776 is in the form of a knurled lock screw that mechanically and selectively engages the locking groove 777 in the sleeve 772. The sheath lock 776 may be rotated to loosen the sheath lock 776 from the locking groove 777 to enable movement of the sleeve 772 and, thus, the drive shaft assembly 140. The sleeve 772 is manipulated by sliding the sleeve 772 relative to the housing 160. Then, once the cutting apparatus 111 has been positioned at a desired location, the sheath lock 776 may be turned to cause the sheath lock 776 to engage the locking groove 777 in the sleeve 772 to lock the drive shaft assembly 140 and, thus, the cutting apparatus 111 (also not shown in FIG. 7) coupled with drive shaft assembly 140 at a desired location. It should be appreciated that other forms of position adjustment apparatuses 170 may be used that include, for example, levers or latches to lock the sleeve 772 in place. It also should be understood that other forms of a position adjustment apparatus 170 may be fixably coupled to a housing of a bronchoscope or other device used to direct the cutting apparatus 111 such that moving the housing results in moving the drive shaft assembly 140. Embodiments of the present disclosure are not limited to use of any particular form of position adjustment apparatus 170.

Still referring to FIG. 7, in some embodiments the rotation grip 180 may include a user grip 781, such as a knurled grip, and an interface 782 that is used to engage a rotation mechanism, such as described below with reference to FIG. 8.

Figure 8:
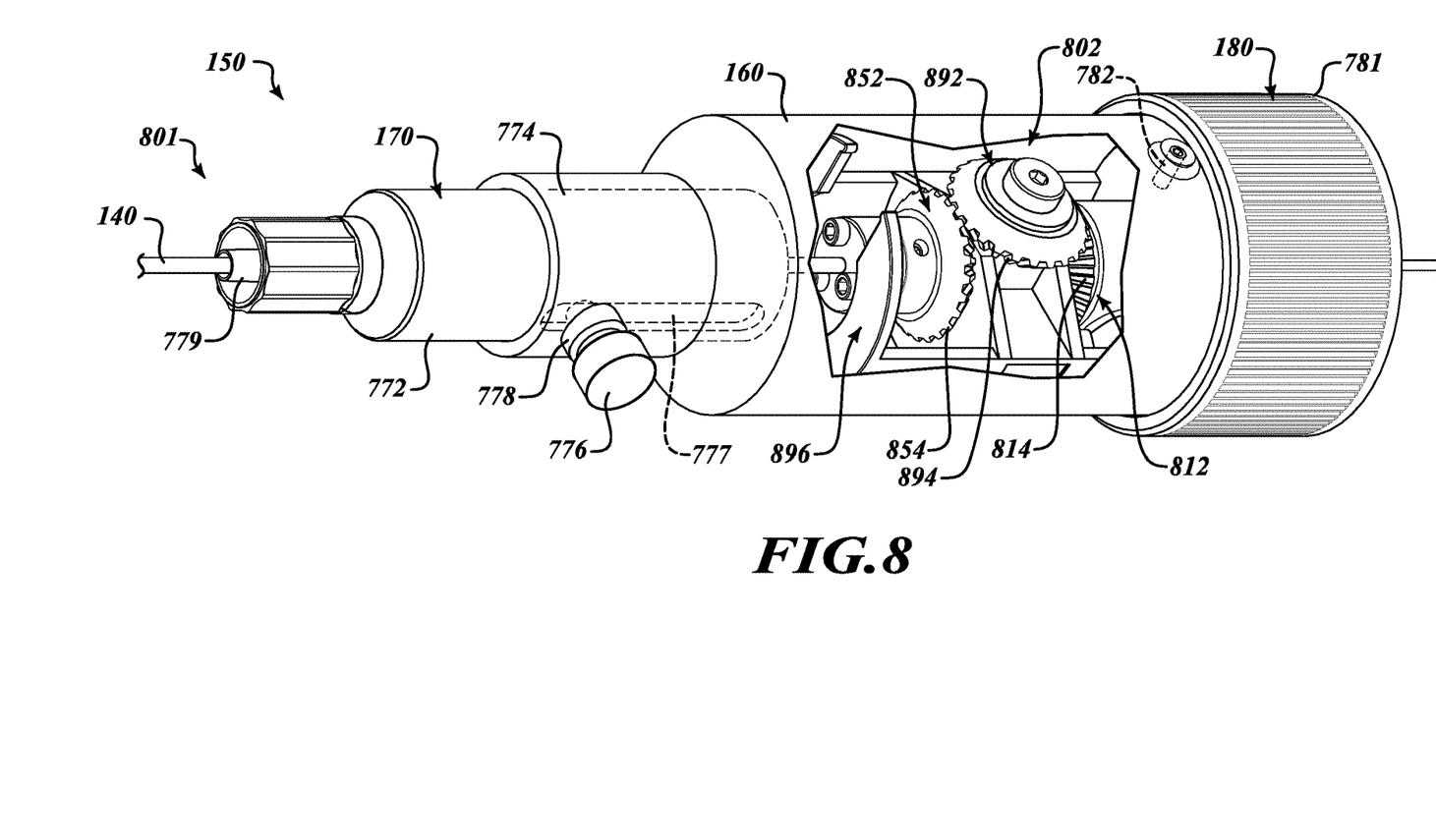
FIG. 8 is a side plan view in cutaway of the apparatus for controlling a counter-rotatable cutting apparatus of the system of FIG. 1.

Referring to FIG. 8, in some embodiments the control apparatus 150 includes a counter-rotating mechanism 802. The counter-rotating mechanism 802 includes a first radial actuator 812 configured to engage a first drive shaft (not shown in FIG. 8) of the drive shaft assembly 140 that, in turn, may be coupled with the inner cutting member 211 of the cutting apparatus 111 (neither of which are shown in FIG. 8). The counter-rotating mechanism 802 includes a second radial actuator 852 configured to engage a second drive shaft (not shown in FIG. 8) of the drive shaft assembly 140 that, in turn, may be coupled with the outer cutting member 251 of the cutting apparatus 111. The configuration of the drive shaft assembly 140 is further described below with reference to FIG. 11.

To cause the drive shafts of the drive shaft assembly 140 to counter-rotate, the first radial actuator 812 and the second radial actuator 852 are mechanically linked to cause the radial actuators 812 and 852 to rotate in opposite directions when one or the other is turned. In the counter-rotating mechanism 802 as shown in FIG. 8, the first radial actuator 812 includes a first beveled gear 814 facing a first end 801 of the housing 160 and the second radial actuator 852 includes a second beveled gear 854 facing away from the first end 801 of the housing 160. Mechanically coupled with each of the first beveled gear 814 and the second beveled gear 854 is a transfer gear 892 that includes a differential beveled gear 894. Rotation of the first beveled gear 814 imparts rotation to the differential beveled gear 894 that causes an opposing rotation to the second beveled gear 854. The counter-rotating mechanism 802 also may include a chassis 896 to support the differential actuators 812 and 854 and the transfer gear 892. As shown in FIG. 8, the first differential actuator 812 receives the interface 782 on the rotation grip 180 so that, when the rotation grip 180 is turned in one direction, the first differential actuator 812 turns in the same direction and the second differential actuator 852 turns in an opposite direction. As a result, drive shafts of the drive shaft assembly 140 relatively counter-rotate, causing the cutting members 211 and 251 of the cutting apparatus 111 to counter-rotate.

Figure 9:
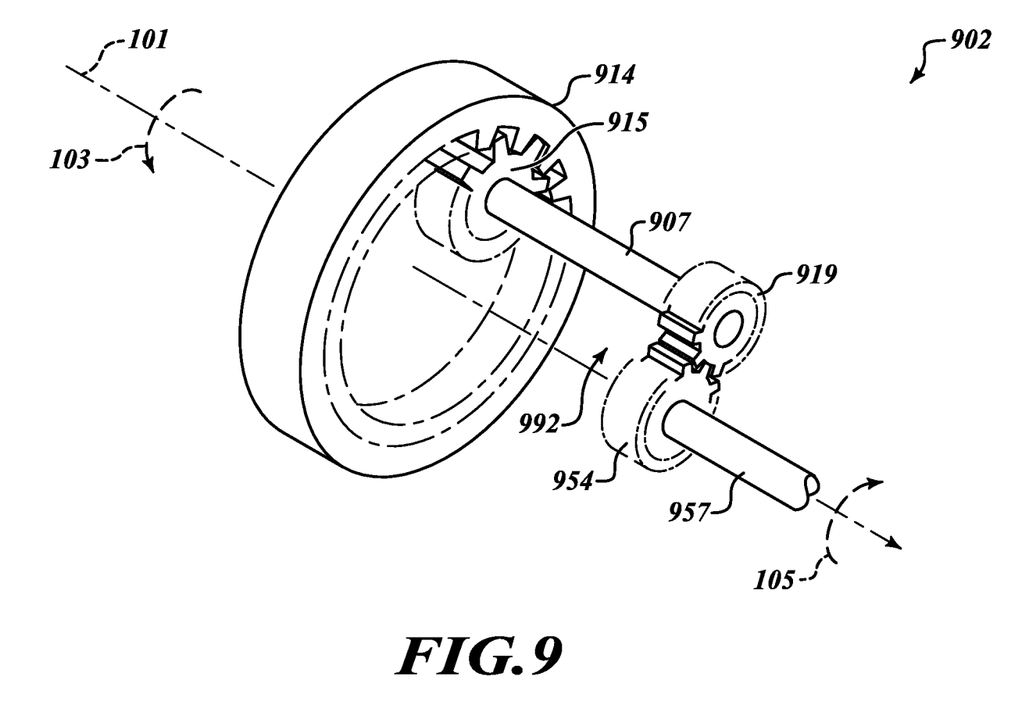
FIG. 9 is a perspective view of another embodiment of a counter-rotating mechanism usable in the apparatus of FIG. 8.

Referring to FIG. 9, another embodiment of a counter-rotating mechanism 902 to facilitate counter-rotation of the drive shafts of the drive shaft assembly 140 and the cutting apparatus 111 (neither of which are shown in FIG. 9) uses spur gears instead of beveled gears as used in the counter-rotating mechanism 802 of FIG. 8. The counter-rotating mechanism 902 includes a base gear 914 that is coupled with the first radial actuator 812 (not shown in FIG. 9) to impart rotation to the base gear 914 when the first radial actuator 812 is rotated as described with reference to FIG. 8. The base gear 914 is an inward-facing spur gear configured to rotate about the axis 101. The base gear 914 engages an axle 992. The axle 992 includes a first transfer gear 915, which may include an outward-facing spur gear. The base gear 914 engages the first transfer gear 915 to impart a rotation to the first transfer gear 915 in a same sense as the rotation of the base gear 914, such as in a direction 103 as shown in FIG. 9. The first radial actuator 812, the base gear 914, or the axle 992 may be coupled to one of the first drive shaft or the second drive shaft (not shown in FIG. 9) to impart rotation to the first drive shaft.

The axle 992 also may include a first shaft 907 that extends to a second transfer gear 919, which also may include an outward-facing spur gear. The first shaft 907, along with other elements shown in FIG. 9, may be rotatably mounted in a cradle (not shown in FIG. 9). Both the first axle 907 and the second transfer gear 919 rotate in a same sense as the first transfer gear 915. The second transfer gear 919 engages a counter-rotating gear 954 that may also may rotatably mounted in a cradle (not shown in FIG. 9). The engagement of the second transfer gear 919 with the counter-rotating gear 954 causes the counter-rotating gear 954 to rotate in an opposite sense as second transfer gear 919 of the axle 992. Thus, for example, if the base gear 914 is rotated in the direction 103, the counter-rotating gear 954 will rotate in the direction 105. The counter-rotating gear 954 may be coupled to a second shaft 957, which may be coupled with the second drive shaft (if the first drive shaft is coupled to the first radial actuator 812 or the base gear 914) or the first drive shaft (if the second drive shaft is coupled to the first radial actuator 812 or the base gear 914). In either case, rotation of the first radial actuator 812 and the base gear 914 in a first direction will result in rotation of the counter-rotating gear 954 in an opposite direction to impart counter-rotation to the cutting members of the cutting apparatus (not shown in FIG. 9).

It should also be appreciated that the counter-rotating mechanism 902 may include a gear differential that enables the base gear 914 to rotate at a different angular velocity from the counter-rotating gear 954. For example, a radius of the first transfer gear 915 and number of spurs extending therefrom relative to a radius of the base gear 914 and a number of spurs extending therefrom changes a rotational speed of the axle 992 relative to the base gear 914. Alternatively or additionally, a radius of the second transfer gear 919 and a number of spurs extending therefrom relative to a radius of the counter-rotating gear 954 and a number of spurs extending therefrom changes a counter-rotational speed of the counter-rotating gear 954 relative to the second transfer gear 919. As a result, the drive shafts (not shown in FIG. 9) may counter-rotate at different speeds, causing the cutting members of the cutting apparatus (also not shown in FIG. 9) to counter-rotate at different speeds. Also, it should be appreciated that while FIG. 9 only shows the spurs extending partially around the circumference of the spur gears to highlight the inter-engagement of the spurs and the associated spur gears, it should be understood that the spurs may extend completely around the circumference of the spur gears.

Figure 10:
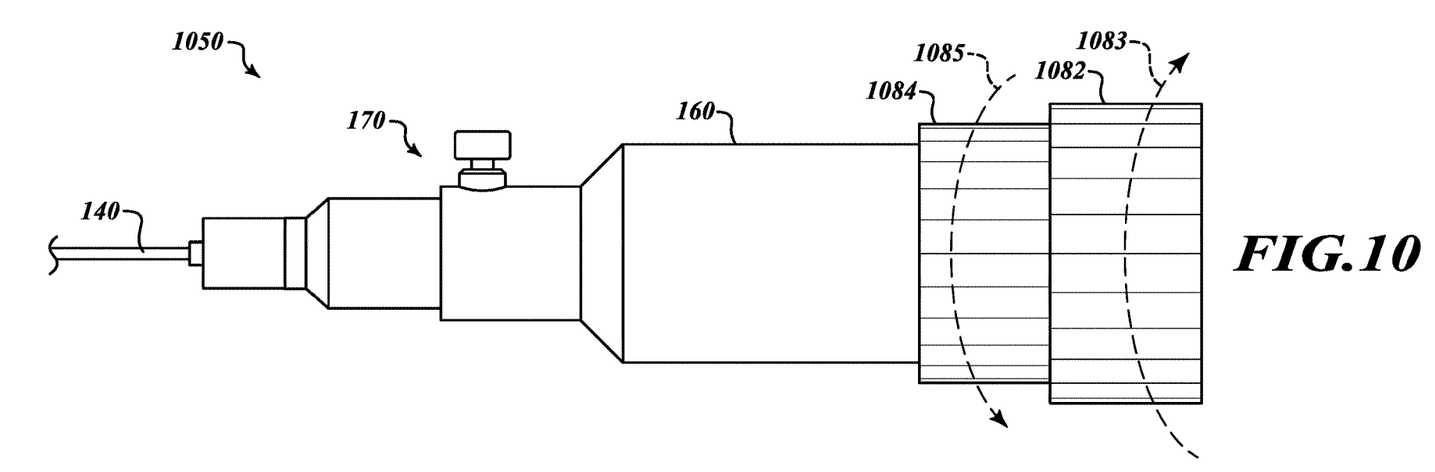
FIG. 10 is a side plan view of another embodiment of the apparatus for controlling a counter-rotatable cutting apparatus of the system of FIG. 1.

Referring to FIG. 10, in some other embodiments a control mechanism 950 includes a housing 160 and a position adjustment apparatus 170 like the control apparatus as shown in FIGS. 7 and 8. However, unlike the control apparatus 150, the control apparatus 1050 includes two rotation grips 1082 and 1084. Each of the rotation grips may be separately coupled with the drive shafts of the drive shaft assembly 140 to effect individual rotation of associated cutting members 211 and 251 of the cutting apparatus 111 (not shown in FIG. 10). Each of the rotation grips 1082 and 1084 may be separately rotated, for example, by rotating a first rotation grip 1082 in a first direction 1083 and by rotating the second rotation grip 1084 in a second direction 1085, to selectively permit individual rotation of the drive shafts of the drive shaft assembly 140 and the associated cutting members 211 and 251 of the cutting apparatus 111 or simultaneous counter-rotation of the associated cutting members 211 and 251 of the cutting apparatus 111.

Figure 11:
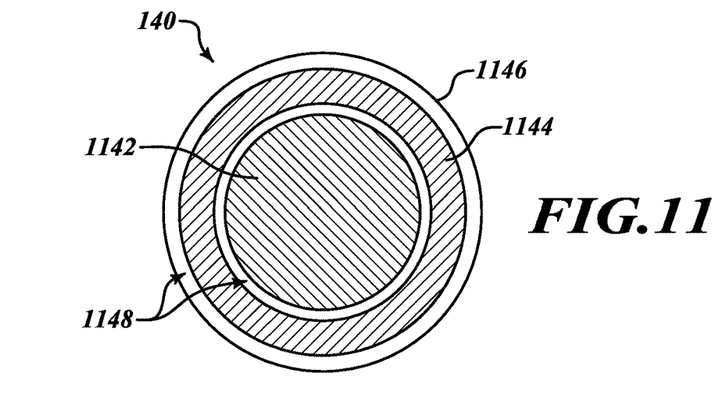
FIG. 11 is a cross-sectional view of a drive shaft assembly of the system of FIG. 1.

Referring to FIG. 11, in various embodiments the drive shaft assembly 140 includes a first drive shaft 1142 that is couplable with the inner cutting member 211 of the cutting apparatus 111 (not shown in FIG. 10). The drive shaft assembly 140 also includes a second drive shaft 1144 that is couplable with the outer cutting member 251 of the cutting apparatus 111. The first drive shaft 1142 may be solid or hollow, while the second drive shaft 1144 is a hollow member coaxially disposed around the first drive shaft 1142. The first drive shaft 1142 and the second drive shaft 1144 are disposed within a sheath 1146 that may be fixably coupled with the sleeve 772 (FIGS. 7 and 8) to permit extension and retraction of the drive shaft assembly 140. The first drive shaft 1142 may be separated from the second drive shaft 1144 by a gap 1148 so as not to impede rotation of the first drive shaft 1142. Similarly, the second drive shaft 1144 may be separated from the sheath 1146 by a gap 1148 so as not to impede rotation of the second drive shaft 1144 by the sheath 1146.

Figure 12:
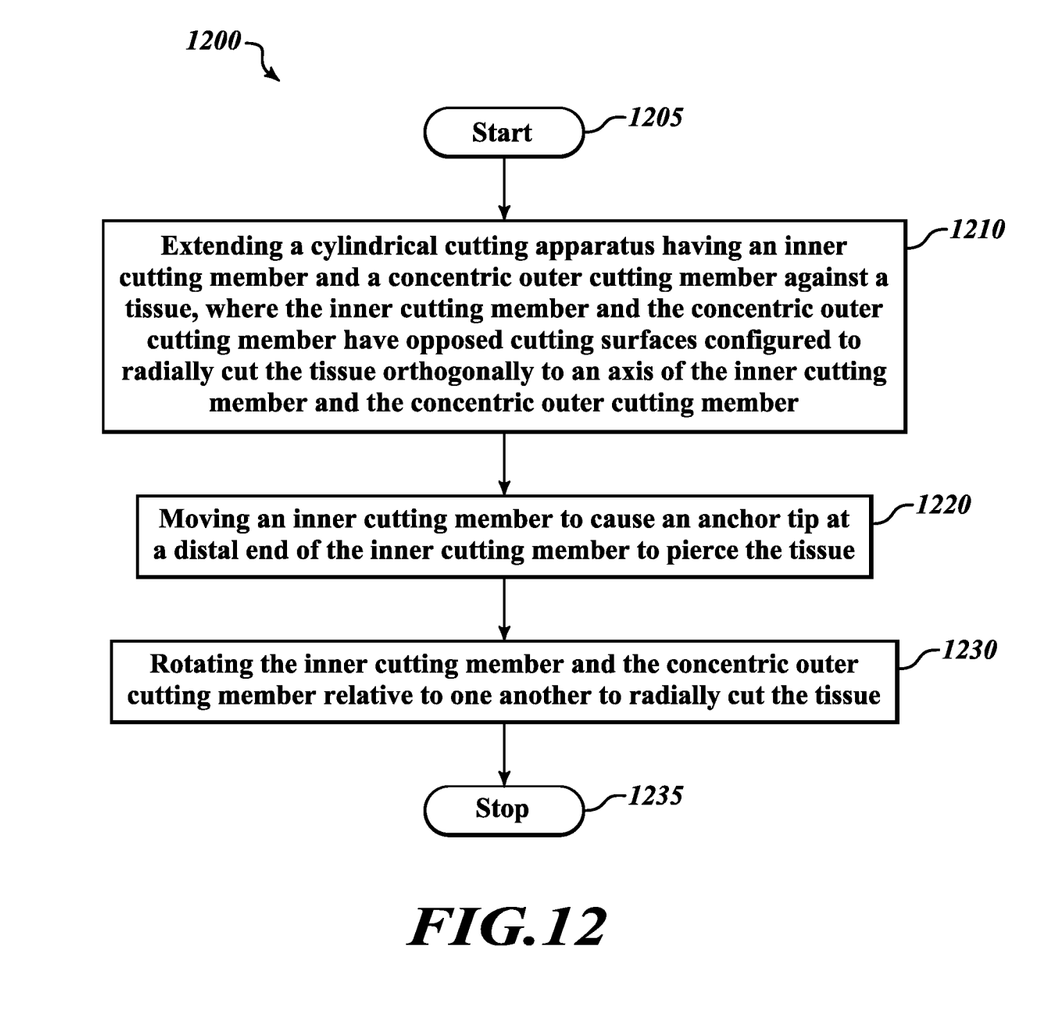
FIG. 12 is a flow diagram of an illustrative method of cutting tissue according to the present disclosure.

Referring to FIG. 12, an illustrative method 1200 of cutting tissue is provided. The method 1200 starts at a block 1205. At a block 1210, a cylindrical cutting apparatus having an inner cutting member and a concentric outer cutting member is extended against a tissue. The inner cutting member and the concentric outer cutting member have opposed cutting surfaces configured to radially cut the tissue orthogonally to an axis of the inner cutting member and the concentric outer cutting member. The configuration of the cutting members and the positioning thereof is previously described with reference to FIGS. 2, 3A-3C, 4A-4C, 5A-5C, and 6.

At a block 1220, an inner cutting member is moved to cause an anchor tip at a distal end of the inner cutting member to pierce the tissue, as previously described with reference to FIGS. 3A-3C, 5A-5C, and 6. At a block 1230, the inner cutting member and the concentric outer cutting member are rotated relative to one another to radially cut the tissue, as previously described in detail with reference to FIG. 6. The method 1200 ends at a block 1235.

It will be appreciated that the present descriptions of the cutting apparatus and control apparatus, as well as systems, and methods described herein as being used for cutting of a hole in a tissue wall may be used for cutting tissue in different parts of a body, and may be guided by endoscopes, bronchoscopes, laparoscopes, or other devices.

It will also be appreciated that the detailed description set forth above is merely illustrative in nature and variations that do not depart from the gist and/or spirit of the claimed subject matter are intended to be within the scope of the claims. Such variations are not to be regarded as a departure from the spirit and scope of the claimed subject matter.

What is claimed is:

1. An apparatus for controlling a counter-rotatable cutting apparatus, the apparatus comprising:
   a first radial actuator configured to engage a first flexible drive shaft;
   a second radial actuator configured to engage a second flexible drive shaft, the second flexible drive shaft being coaxially disposed with the first flexible drive shaft; and
   a housing supporting the first radial actuator and the second radial actuator and permitting the first flexible drive shaft and the second flexible drive shaft to extend therethrough, the first flexible drive shaft and the second flexible drive shaft being relatively counter-rotatable responsive to rotation of at least one of the first radial actuator and the second radial actuator.

2. The apparatus of claim 1, further comprising a counter-rotating mechanism that mechanically couples the first radial actuator and the second radial actuator, the counter-rotating mechanism being configured to cause the second radial actuator to rotate in a second direction when the first radial actuator is turned in a first direction.

3. The apparatus of claim 2, wherein the counter-rotating mechanism includes a plurality of gears counter-rotationally coupling the first radial actuator and the second radial actuator, the first radial actuator and the second radial actuator being simultaneously counter-rotatable responsive to rotation of at least one of the first radial actuator and the second radial actuator.

4. The apparatus of claim 3, wherein the plurality of gears includes a plurality of spur gears.

5. The apparatus of claim 3, wherein the counter-rotating mechanism includes a gear differential mechanically coupled between the first radial actuator and the second radial actuator causing the first radial actuator and the second radial actuator to counter-rotate at different rotational speeds.

6. The apparatus of claim 3, wherein the counter-rotating mechanism includes:
a first beveled gear coupled to the first radial actuator, wherein a first beveled face of the first beveled gear faces the second radial actuator;
a second beveled gear coupled to the second radial actuator, wherein a second beveled face of the second beveled gear faces the first radial actuator; and
a differential beveled gear configured to engage the first beveled face of the first beveled gear and the second beveled face of the second beveled gear.

7. The apparatus of claim 2, further comprising a first rotation control extending radially from the housing and fixably coupled to the first radial actuator, the first radial actuator and the second radial actuator being simultaneously counter-rotatable responsive to rotation of the first rotation control.

8. The apparatus of claim 1, further comprising a first rotation control extending radially from the housing and fixably coupled to the first radial actuator and a second rotation control extending radially from the housing and fixably coupled to the second radial actuator, the first radial actuator and the second radial actuator being counter-rotatable responsive to counter-rotation of the first rotation control and the second rotation control.

9. An apparatus for controlling a counter-rotatable cutting apparatus, the apparatus comprising:
a first radial actuator configured to engage a first flexible drive shaft;
a second radial actuator configured to engage a second flexible drive shaft, the second flexible drive shaft being coaxially disposed with the first flexible drive shaft;
a counter-rotating mechanism that mechanically couples the first radial actuator and the second radial actuator, the counter-rotating mechanism being configured to cause the second radial actuator to rotate in a second direction when the first radial actuator is turned in a first direction;
a sheath containing the first flexible drive shaft and the second flexible drive shaft;
a housing supporting the first radial actuator and the second radial actuator and configured to permit the sheath containing the first flexible drive shaft and the second flexible drive shaft extend therethrough while preventing rotation of the sheath; and
a rotation control mechanically coupled with the first radial actuator to permit rotation of the first radial actuator, the first flexible drive shaft and the second flexible drive shaft being simultaneously counter-rotatable responsive to rotation of the first rotation control.

10. The apparatus of claim 9, wherein the counter-rotating mechanism includes a plurality of gears counter-rotationally coupling the first radial actuator and the second radial actuator, the first radial actuator and the second radial actuator being simultaneously counter-rotatable responsive to rotation of at least one of the first radial actuator and the second radial actuator.

11. The apparatus of claim 10, wherein the plurality of gears includes a plurality of spur gears.

12. The apparatus of claim 10, wherein the counter-rotating mechanism includes a gear differential mechanically coupled between the first radial actuator and the second radial actuator causing the first radial actuator and the second radial actuator to counter-rotate at different rotational speeds.

13. The apparatus of claim 10, wherein the counter-rotating mechanism includes:
a first beveled gear coupled to the first radial actuator, wherein a first beveled face of the first beveled gear faces the second radial actuator;
a second beveled gear coupled to the second radial actuator, wherein a second beveled face of the second beveled gear faces the first radial actuator; and
a differential beveled gear configured to engage the first beveled face of the first beveled gear and the second beveled face of the second beveled gear, the first beveled gear and the second beveled gear being relatively counter-rotatable responsive to rotation of the rotation control.

14. A system for cutting tissue, the system comprising:
a drive shaft assembly, including:
a first drive shaft;
a second drive shaft coaxially disposed around the first drive shaft and configured to rotate independently of the first drive shaft; and
a sheath containing the first drive shaft and the second drive shaft;
a first radial actuator configured to engage the first drive shaft;
a second radial actuator configured to engage the second drive shaft;
a housing supporting the first radial actuator and the second radial actuator and permitting the sheath containing the first drive shaft and the second drive shaft to extend therethrough;
a rotation control mechanically coupled with the first radial actuator to permit rotation of the first radial actuator relative to the second radial actuator; and
a cutting apparatus including:
an inner cutting member having a first cylindrical body supporting at least one first cutting surface at a distal end of the cutter and mechanically coupled to the first drive shaft, wherein the first cutting surface faces a first rotational direction relative to an axis of the first cylindrical body and has a first cutting edge at an outer periphery of the first cylindrical body; and
an outer cutting member having a second cylindrical body concentrically disposed around the first cylindrical body and mechanically coupled with the second drive shaft, wherein the outer cutting member supports at least one second cutting surface at the distal end of the apparatus and the second cutting surface faces a second rotational direction relative to the axis and has a second cutting edge at an inner periphery of the second cylindrical body, a tissue being rotatably scissorable between the first cutting edge of the inner cutting member and the second cutting edge of the outer cutting member responsive to application of the distal end of the apparatus and rotation of the rotation control.

15. The system of claim 14, further comprising a counter-rotating mechanism that mechanically couples the first radial actuator and the second radial actuator, the counter-rotating mechanism being configured to cause the second radial actuator to rotate in a second direction when the first radial actuator is turned in a first direction.

16. The system of claim 15, wherein the counter-rotating mechanism includes a plurality of gears counter-rotationally coupling the first radial actuator and the second radial actuator, the first radial actuator and the second radial actuator being simultaneously counter-rotatable responsive to rotation of at least one of the first radial actuator and the second radial actuator.

17. The system of claim 16, wherein the plurality of gears includes a plurality of spur gears.

18. The system of claim 16, wherein the counter-rotating mechanism includes a gear differential mechanically coupled between the first radial actuator and the second radial actuator causing the first radial actuator and the second radial actuator to counter-rotate at different rotational speeds.

19. The system of claim 16, wherein the counter-rotating mechanism includes:
- a first beveled gear coupled to the first radial actuator, wherein a first beveled face of the first beveled gear faces the second radial actuator;
- a second beveled gear coupled to the second radial actuator, wherein a second beveled face of the second beveled gear faces the first radial actuator; and
- a differential beveled gear configured to engage the first beveled face of the first beveled gear and the second beveled face of the second beveled gear.

* * * * *